(12) United States Patent
Brunkow et al.

(10) Patent No.: US 6,884,618 B2
(45) Date of Patent: *Apr. 26, 2005

(54) IDENTIFICATION OF THE GENE CAUSING THE MOUSE SCURFY PHENOTYPE AND ITS HUMAN ORTHOLOG

(75) Inventors: Mary E. Brunkow, Seattle, WA (US); Eric W. Jeffery, Seattle, WA (US); Kathryn A. Hjerrild, Bainbridge Island, WA (US); Fred Ramsdell, Bainbridge Island, WA (US)

(73) Assignee: Darwin Discovery Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/115,195

(22) Filed: Apr. 2, 2002

(65) Prior Publication Data

US 2002/0168736 A1 Nov. 14, 2002

Related U.S. Application Data

(63) Continuation of application No. 09/372,668, filed on Aug. 11, 1999, now Pat. No. 6,414,129.
(60) Provisional application No. 60/096,195, filed on Aug. 11, 1998, now abandoned.

(51) Int. Cl.[7] .......................... C12N 5/00; C12N 15/00; C12N 15/63; C07H 21/02; C07H 21/04
(52) U.S. Cl. .................. 435/320.1; 435/69.1; 435/325; 435/455; 536/23.1; 536/23.5
(58) Field of Search ............................ 435/69.1, 320.1, 435/325, 455; 536/23.1, 23.5; 530/350

(56) References Cited

U.S. PATENT DOCUMENTS

6,414,129 B1 * 7/2002 Brunkow et al. .......... 536/23.5

FOREIGN PATENT DOCUMENTS

WO    WO 98/45435    10/1998

OTHER PUBLICATIONS

Brunkow et al Disruption of a new forkhead/winged–helix protein, scurfin, results in the fatal lymphoproliferative disorder of the scurfy mouse Nat Genet. 27(1):68–73, 2001.*
Ngo, Computational complexity Protein structure prediction and the Levinthal paradox in The Protein Folding Problem and Tertiary Structure Prediction, Merz et al. (eds.), Burkhauser Boston: Boston, MA, pp. 433 and 492–495, 1994).*
Rudinger Characteristics of amino acids as components of a peptide hormone sequence (in Peptide Hormones, Parsons (eds.), University Park Press: Baltimore, MD, pp. 1–7, 1976).*

Barbosa et al., "Identification of the Homologous Beige and Chediak–Higashi Syndrome Genes," *Nature* 382:262–265, 1996.
Bignon and Siminovitch, "Identification of PTP1C Mutations as the Genetic Defect in Motheaten and Viable Motheaten Mice: A Step Toward Defining the Roles of Protein Tyrosine Phosphatases in the Regulation of Hemopoietic Cell Differentiation and Function," *Clinical Immunology and Immunopathology* 73(2):168–179, 1994.
Blair et al., "The Mouse Scurfy (sf) Mutation Is Tightly Linked to *GataI* and *Tfe3* on the Proximal X Chromosome," *Mammalian Genome* 5:652–654, 1994.
Database Genbank Accession No. AI949471, Aug. 1, 1998.
Database Genbank Accession No. AJ005891, May 1, 1998.
Derry et al., "The Mouse Homolog of the Wiskott–Aldrich Syndrome Protein (WASP) Gene Is Highly Conserved and Maps near the Scurfy (sf) Mutation on the X Chromosome," *Genomics* 29:471–477, 1995.
Godfrey et al., "Fatal Lymphoreticular Disease in the Scurfy (sf) Mouse Requires T Cells that Mature in a *sf* Thymic Environment: Potential Model for Thymic Education," *Proc. Natl. Acad. Sci. USA* 88:5528–5532, 1991.
Godfrey et al., "X–Linked Lymphoreticular Disease in the Scurfy (*sf*) Mutant Mouse," *American Journal of Pathology* 138(6):1379–1387, 1991.
Lyon et al., "The Scurfy Mouse Mutant has Previously Unrecognized Hematological Abnormalities and Resembles Wiskott–Aldrich Syndrome," *Proc. Natl. Acad. Sci. USA* 87:2433–2437, 1990.
Rawlings et al., "Mutation of Unique Region of Bruton's Tyrosine Kinase in Immunodeficient XID Mice," *Science* 261:358–361, 1993.
Sugamura et al., "The Interleukin–2 Receptor γ Chain: Its Role in the Multiple Cytokine Receptor Complexes and T Cell Development in XSCID," *Ann. Rev. Immuno.* 14:179–205, 1996.
Veres et al., "The Molecular Basis of the Sparse Fur Mouse Mutation," *Science* 237:415–417, 1987.
Strom et al., GenEmbl database, Accession No. AJ005891, 1998.

* cited by examiner

*Primary Examiner*—Jeffrey Fredman
*Assistant Examiner*—Sumesh Kaushal
(74) *Attorney, Agent, or Firm*—Davis Wright Tremaine LLP; Jane E. R. Potter

(57) ABSTRACT

Isolated nucleic acid molecules are provided which encode Fkh$^{sf}$, as well as mutant forms thereof. Also provided are expression vectors suitable for expressing such nucleic acid molecules, and host cells containing such expression vectors. Utilizing assays based upon the nucleic acid sequences disclosed herein (as well as mutant forms thereof), numerous molecules may be identified which modulate the immune system.

6 Claims, 11 Drawing Sheets

MOUSE *Fkh*<sup>sf</sup> cDNA SEQUENCE

```
   1  GCTGATCCCC CTCTAGCAGT CCACTTCACC AAGGTGAGCG AGTGTCCCTG
  51  CTCTCCCCCA CCAGACACAG CTCTGCTGGC GAAAGTGGCA GAGAGGTATT
 101  GAGGGTGGGT GTCAGGAGCC CACCAGTACA GCTGGAAACA CCCAGCCACT
 151  CCAGCTCCCG GCAACTTCTC CTGACTCTGC CTTCAGACGA GACTTGGAAG
 201  ACAGTCACAT CTCAGCAGCT CCTCTGCCGT TATCCAGCCT GCCTCTGACA
 251  AGAACCCAAT GCCCAACCCT AGGCCAGCCA AGCCTATGGC TCCTTCCTTG
 301  GCCCTTGGCC CATCCCCAGG AGTCTTGCCA AGCTGGAAGA CTGCACCCAA
 351  GGGCTCAGAA CTTCTAGGGA CCAGGGGCTC TGGGGGACCC TTCCAAGGTC
 401  GGGACCTGCG AAGTGGGGCC CACACCTCTT CTTCCTTGAA CCCCCTGCCA
 451  CCATCCCAGC TGCAGCTGCC TACAGTGCCC CTAGTCATGG TGGCACCGTC
 501  TGGGGCCCGA CTAGGTCCCT CACCCCACCT ACAGGCCCTT CTCCAGGACA
 551  GACCACACTT CATGCATCAG CTCTCCACTG TGGATGCCCA TGCCCAGACC
 601  CCTGTGCTCC AAGTGCGTCC ACTGGACAAC CCAGCCATGA TCAGCCTCCC
 651  ACCACCTTCT GCTGCCACTG GGTCTTCTC CCTCAAGGCC CGGCCTGGCC
 701  TGCCACCTGG GATCAATGTG GCCAGTCTGG AATGGGTGTC CAGGGAGCCA
 751  GCTCTACTCT GCACCTTCCC ACGCTCGGGT ACACCCAGGA AAGACAGCAA
 801  CCTTTTGGCT GCACCCCAAG GATCCTACCC ACTGCTGGCA AATGGAGTCT
 851  GCAAGTGGCC TGGTTGTGAG AAGGTCTTCG AGGAGCCAGA AGAGTTTCTC
 901  AAGCACTGCC AAGCAGATCA TCTCCTGGAT GAGAAAGGCA AGGCCCAGTG
 951  CCTCCTCCAG AGAGAAGTGG TGCAGTCTCT GGAGCAGCAG CTGGAGCTGG
1001  AAAAGGAGAA GCTGGGAGCT ATGCAGGCCC ACCTGGCTGG GAAGATGGCG
1051  CTGGCCAAGG CTCCATCTGT GGCCTCAATG GACAAGAGCT CTTGCTGCAT
1101  CGTAGCCACC AGTACTCAGG GCAGTGTGCT CCCGGCCTGG TCTGCTCCTC
```

*Fig. 1A*

```
1101  CGTAGCCACC AGTACTCAGG GCAGTGTGCT CCCGGCCTGG TCTGCTCCTC
1151  GGGAGGCTCC AGACGGCGGC CTGTTTGCAG TGCGGAGGCA CCTCTGGGGA
1201  AGCCATGGCA ATAGTTCCTT CCCAGAGTTC TTCCACAACA TGGACTACTT
1251  CAAGTACCAC AATATGCGAC CCCCTTTCAC CTATGCCACC CTTATCCGAT
1301  GGGCCATCCT GGAAGCCCCG GAGAGGCAGA GGACACTCAA TGAAATCTAC
1351  CATTGGTTTA CTCGCATGTT CGCCTACTTC AGAAACCACC CCGCCACCTG
1401  GAAGAATGCC ATCCGCCACA ACCTGAGCCT GCACAAGTGC TTTGTGCGAG
1451  TGGAGAGCGA GAAGGGAGCA GTGTGGACCG TAGATGAATT TGAGTTTCGC
1501  AAGAAGAGGA GCCAACGCCC CAACAAGTGC TCCAATCCCT GCCCTTGACC
1551  TCAAAACCAA GAAAAGGTGG GCGGGGGAGG GGGCCAAAAC CATGAGACTG
1601  AGGCTGTGGG GGCAAGGAGG CAAGTCCTAC GTGTACCTAT GGAAACCGGG
1651  CGATGATGTG CCTGCTATCA GGGCCTCTGC TCCCTATCTA GCTGCCCTCC
1701  TAGATCATAT CATCTGCCTT ACAGCTGAGA GGGGTGCCAA TCCCAGCCTA
1751  GCCCCTAGTT CCAACCTAGC CCAAGATGA ACTTTCCAGT CAAAGAGCCC
1801  TCACAACCAG CTATACATAT CTGCCTTGGC CACTGCCAAG CAGAAAGATG
1851  ACAGACACCA TCCTAATATT TACTCAACCC AAACCCTAAA ACATGAAGAG
1901  CCTGCCTTGG TACATTCGTG AACTTTCAAA GTTAGTCATG CAGTCACACA
1951  TGACTGCAGT CCTACTGACT CACACCCCAA AGCACTCACC CACAACATCT
2001  GGAACCACGG GCACTATCAC ACATAGGTGT ATATACAGAC CCTTACACAG
2051  CAACAGCACT GGAACCTTCA CAATTACATC CCCCCAAACC ACACAGGCAT
2101  AACTGATCAT ACGCAGCCTC AAGCAATGCC CAAAATACAA GTCAGACACA
2151  GCTTGTCAGA
```

*Fig. 1B*

MOUSE Fkh$^{sf}$ PROTEIN SEQUENCE

```
  1  MPNPRPAKPM APSLALGPSP GVLPSWKTAP KGSELLGTRG SGGPFQGRDL
 51  RSGAHTSSSL NPLPPSQLQL PTVPLVMVAP SGARLGPSPH LQALLQDRPH
101  FMHQLSTVDA HAQTPVLQVR PLDNPAMISL PPPSAATGVF SLKARPGLPP
151  GINVASLEWV SREPALLCTF PRSGTPRKDS NLLAAPQGSY PLLANGVCKW
201  PGCEKVFEEP EEFLKHCQAD HLLDEKGKAQ CLLQREVVQS LEQQLELEKE
251  KLGAMQAHLA GKMALAKAPS VASMDKSSCC IVATSTQGSV LPAWSAPREA
301  PDGGLFAVRR HLWGSHGNSS FPEFFHNMDY FKYHNMRPPF TYATLIRWAI
351  LEAPERQRTL NEIYHWFTRM FAYFRNHPAT WKNAIRHNLS LHKCFVRVES
401  EKGAVWTVDE FEFRKKRSQR PNKCSNPCP*
```

*Fig. 2*

HUMAN $FKH^{sf}$ cDNA Sequence

```
   1  GCACACACTC ATCGAAAAAA ATTTGGATTA TTAGAAGAGA GAGGTCTGCG
  51  GCTTCCACAC CGTACAGCGT GGTTTTTCTT CTCGGTATAA AAGCAAAGTT
 101  GTTTTTGATA CGTGACAGTT TCCCACAAGC CAGGCTGATC CTTTTCTGTC
 151  AGTCCACTTC ACCAAGCCTG CCCTTGGACA AGGACCCGAT GCCCAACCCC
 201  AGGCCTGGCA AGCCCTCGGC CCCTTCCTTG GCCCTTGGCC CATCCCCAGG
 251  AGCCTCGCCC AGCTGGAGGG CTGCACCCAA AGCCTCAGAC CTGCTGGGGG
 301  CCCGGGGCCC AGGGGGAACC TTCCAGGGCC GAGATCTTCG AGGCGGGGCC
 351  CATGCCTCCT CTTCTTCCTT GAACCCCATG CCACCATCGC AGCTGCAGCT
 401  GCCCACACTG CCCCTAGTCA TGGTGGCACC CTCCGGGGCA CGGCTGGGCC
 451  CCTTGCCCCA CTTACAGGCA CTCCTCCAGG ACAGGCCACA TTTCATGCAC
 501  CAGCTCTCAA CGGTGGATGC CCACGCCCGG ACCCTGTGC TGCAGGTGCA
 551  CCCCTGGAG AGCCCAGCCA TGATCAGCCT CACACCACCC ACCACCGCCA
 601  CTGGGGTCTT CTCCCTCAAG GCCCGGCCTG GCCTCCCACC TGGGATCAAC
 651  GTGGCCAGCC TGGAATGGGT GTCCAGGGAG CCGGCACTGC TCTGCACCTT
 701  CCCAAATCCC AGTGCACCCA GGAAGGACAG CACCCTTTCG GCTGTGCCCC
 751  AGAGCTCCTA CCCACTGCTG GCAAATGGTG TCTGCAAGTG GCCCGGATGT
 801  GAGAAGGTCT TCGAAGAGCC AGAGGACTTC CTCAAGCACT GCCAGGCGGA
 851  CCATCTTCTG GATGAGAAGG GCAGGGCACA ATGTCTCCTC CAGAGAGAGA
 901  TGGTACAGTC TCTGGAGCAG CAGCTGGTGC TGGAGAAGGA GAAGCTGAGT
 951  GCCATGCAGG CCCACCTGGC TGGGAAAATG GCACTGACCA AGGCTTCATC
1001  TGTGGCATCA TCCGACAAGG CTCCTGCTG CATCGTAGCT GCTGGCAGCC
1051  AAGGCCCTGT CGTCCCAGCC TGGTCTGGCC CCCGGGAGGC CCCTGACAGC
1101  CTGTTTGCTG TCCGGAGGCA CCTGTGGGGT AGCCATGGAA ACAGCACATT
```

*Fig. 3A*

```
1151  CCCAGAGTTC CTCCACAACA TGGACTACTT CAAGTTCCAC AACATGCGAC
1201  CCCCTTTCAC CTACGCCACG CTCATCCGCT GGGCCATCCT GGAGGCTCCA
1251  GAGAAGCAGC GGACACTCAA TGAGATCTAC CACTGGTTCA CACGCATGTT
1301  TGCCTTCTTC AGAAACCATC CTGCCACCTG GAAGAACGCC ATCCGCCACA
1351  ACCTGAGTCT GCACAAGTGC TTTGTGCGGG TGGAGAGCGA GAAGGGGGCT
1401  GTGTGGACCG TGGATGAGCT GGAGTTCCGC AAGAAACGGA GCCAGAGGCC
1451  CAGCAGGTGT TCCAACCCTA CACCTGGCCC CTGACCTCAA GATCAAGGAA
1501  AGGAGGATGG ACGAACAGGG GCCAAACTGG TGGGAGGCAG AGGTGGTGGG
1551  GGCAGGGATG ATAGGCCCTG GATGTGCCCA CAGGGACCAA GAAGTGAGGT
1601  TTCCACTGTC TTGCCTGCCA GGGCCCTGT TCCCCGCTG GCAGCCACCC
1651  CCTCCCCCAT CATATCCTTT GCCCCAAGGC TGCTCAGAGG GGCCCCGGTC
1701  CTGGCCCCAG CCCCCACCTC CGCCCCAGAC ACACCCCCA GTCGAGCCCT
1751  GCAGCCAAAC AGAGCCTTCA CAACCAGCCA CACAGAGCCT GCCTCAGCTG
1801  CTCGCACAGA TTACTTCAGG GCTGGAAAAG TCACACAGAC ACACAAAATG
1851  TCACAATCCT GTCCCTCAC
```

*Fig. 3B*

HUMAN FKH$^{sf}$ PROTEIN SEQUENCE

```
  1  MPNPRPGKPS APSLALGPSP GASPSWRAAP KASDLLGARG PGGTFQGRDL
 51  RGGAHASSSS LNPMPPSQLQ LPTLPLVMVA PSGARLGPLP HLQALLQDRP
101  HFMHQLSTVD AHARTPVLQV HPLESPAMIS LTPPTTATGV FSLKARPGLP
151  PGINVASLEW VSREPALLCT FPNPSAPRKD STLSAVPQSS YPLLANGVCK
201  WPGCEKVFEE PEDFLKHCQA DHLLDEKGRA QCLLQREMVQ SLEQQLVLEK
251  EKLSAMQAHL AGKMALTKAS SVASSDKGSC CIVAAGSQGP VVPAWSGPRE
301  APDSLFAVRR HLWGSHGNST FPEFLHNMDY FKFHNMRPPF TYATLIRWAI
351  LEAPEKQRTL NEIYHWFTRM FAFFRNHPAT WKNAIRHNLS LHKCFVRVES
401  EKGAVWTVDE LEFRKKRSQR PSRCSNPTPG P*
```

*Fig. 4*

FKHsf Transgene corrects the defect in scurfy animals

FKHsf tg mice have reduce lymph node cells
compared to normal cells

| Cell number | Mouse genotype | | |
|---|---|---|---|
| | Normal | Scurfy | Transgenic |
| Cells / LN | 0.92 | 1.97 | 0.29 |
| Cells / Thymus | 0.76 | 0.54 | 0.76 |

*Fig. 7*

FKHsf trangenic mice respond poorly to in vitro stimulation

| Proliferation | Mouse genotype | | |
|---|---|---|---|
| | Normal | Scurfy | Transgenic |
| No stimulation | 778 | 23488 | 596 |
| Anti-CD3+Anti-CD28 | 22932 | 225981 | 9106 |

*Fig. 8*

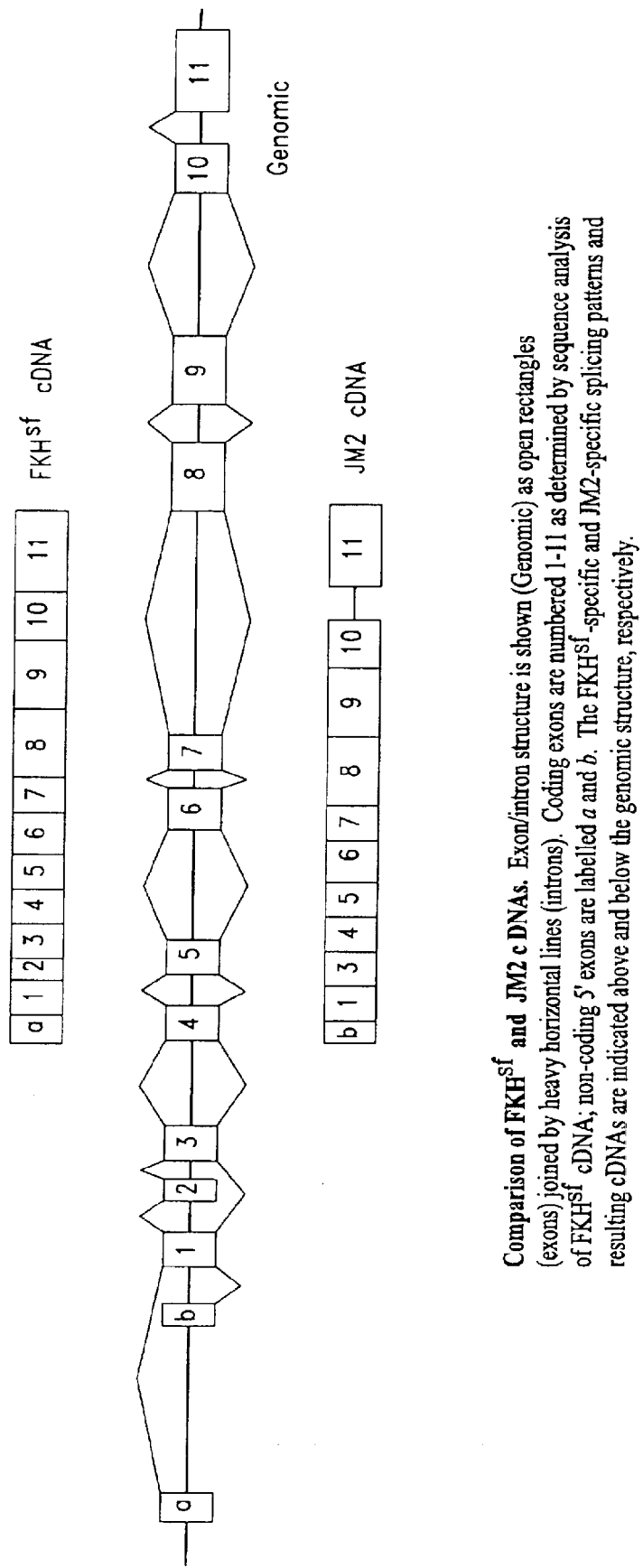

Comparison of FKH$^{sf}$ and JM2 cDNAs. Exon/intron structure is shown (Genomic) as open rectangles (exons) joined by heavy horizontal lines (introns). Coding exons are numbered 1-11 as determined by sequence analysis of FKH$^{sf}$ cDNA; non-coding 5' exons are labelled a and b. The FKH$^{sf}$-specific and JM2-specific splicing patterns and resulting cDNAs are indicated above and below the genomic structure, respectively.

Fig. 9

| N-terminal | ZNF | Mid | Forkhead | Human FKHsf |
|---|---|---|---|---|
| 83.4% | 95.8% | 82.8% | 96.4% | |
| | | | | Mouse Fkhsf |

Human and mouse FKHsf proteins are highly conserved.

IDENTIFICATION OF THE GENE CAUSING THE MOUSE SCURFY PHENOTYPE AND ITS HUMAN ORTHOLOG

CROSS-REFERENCE TO RELATED APPLICATIONS

This application is a continuation of U.S. patent application Ser. No. 09/372,668 filed Aug. 11, 1999, now U.S. Pat. No. 6,414,129, which application claims the benefit of U.S. Provisional Patent Application No. 60/096,195, filed Aug. 11, 1998, now abandoned where these applications are incorporated herein by reference in their entireties.

TECHNICAL FIELD

The present invention relates generally to pharmaceutical products and methods and, more specifically. to methods and compositions useful for diagnosing scurfy-related diseases, as well as methods for identifying compounds which can modulate the immune system.

BACKGROUND OF THE INVENTION

Inherited mutations affecting the murine immune system have proven to be a rich source of novel genes critical to the regulation of the immune system and have furnished important animal models for human immunological disorders. These include xid, the murine equivalent of X-linked agammaglobulinemia (Thomas et al., *Science* 261:355, 1993; Rawlings et al., *Science* 261:358, 1993), beige (the equivalent of Chediak-Higashi Syndrome) (Barbosa et al., *Nature* 382:262, 1996), lpr and gld (defects in fas and fas-ligand), X-linked severe combined immunodeficiency (Sugamura et al., *Annu. Rev. Immunol* 14:179, 1996), and the hematopoietic cell phosphatase mutant motheaten (SHP-1) (Bignon and Siminovitch, *Clin Immunol Immunopathol* 73:168, 1994).

One mouse mutant of particular interest is the as-yet uncloned X-linked mouse mutant, scurfy (sf). Briefly, mice hemizygous for the scurfy mutation exhibit a severe lymphoproliferative disorder. In particular, males hemizygous ($X^{sf}/Y$) for the scurfy mutation develop a progressive lymphocytic infiltration of the lymph nodes. spleen, liver and skin resulting in gross morphological symptoms which include splenomegaly, hepatomegaly, greatly enlarged lymph nodes, runting, exfoliative dermatitis, and thickened malformed ears (Godfrey et al., *Amer. J. Pathol.* 138:1379, 1991; Godfrey et al., *Proc. Natl. Acad. Sci. USA* 88:5528, 1991). Other clinical symptoms include elevated leukocyte counts. hypergarnraglobulinemia, and severe anemia (Lyon et al., *Proc. Natl. Acad. Sci. USA* 87:2433, 1990); the death of affected males usually occurs by 3 weeks of age. The sf locus has been mapped to the extreme proximal region of the X chromosome, approximately 0.7 centimorgans from the locus for sparse-fur (spf) (Lyon et al., *Proc. Natl. Acad. Sci. USA* 87:2433, 1990; Blair et al., *Mamm. Genome* 5:652, 1994), itself a point mutation within the ornithine transcarbamylase gene (Otc) (Veres et al., *Science* 237:415, 1987). The sf locus is also tightly linked to the murine Gata1, Tcfe3, and Wasp loci (Blair et al., *Mamm. Genome* 5:652, 1994; Derry et al., *Genomics* 29:471. 1995). Similarities between scurfy and human Wiskott-Aldrich syndrome (WAS) have been noted (Lyon et al., *Proc. Natl. Acad. Sci. USA* 87:2433, 1990), and the mouse Wasp gene has been proposed as a candidate for scurfy (Lyon et al., *Proc. Natl. Acad. Sci. USA* 87:2433, 1990; Derry et al., *Genomics* 29:471, 1995). Closer biological examination reveals significant differences between WAS and scurfy, however, and the two loci have been demonstrated to be non-allelic (Jeffery & Brunkow, unpublished data). Thus, prior to applicants' invention the identity of the scurfy gene remained to be determined.

The present invention discloses methods and compositions useful for diagnosing scurfy-related diseases, as well as methods for identifying compounds which can modulate the immune system, and further provides other related advantages.

SUMMARY OF THE INVENTION

The present invention relates generally to the discovery of novel genes which, when mutated, results in a profound lymphoproliferative disorder. In particular, a mutant mouse, designated Scurfy, was used to identify the gene responsible for this disorder through backcross analysis, physical mapping and large-scale DNA sequencing. Analysis of the sequence of this gene indicated that it belongs to a family of related genes, all containing a winged-helix DNA binding domain.

Thus, within one aspect of the invention isolated nucleic acid molecules are provided which encode $FKH^{sf}$ or $Fkh^{sf}$, including mutant forms thereof. Within certain embodiments, $Fkh^{sf}$ of any type may be from a warm-blooded animal, such as a mouse or human. Within farther embodiments, isolated nucleic acid molecules are provided wherein the nucleic acid molecule is selected from the group consisting of (a) a nucleic acid molecule that encodes an amino acid sequence comprising SEQ ID Nos 2, or, 4, (b) a nucleic acid molecule that hybridizes under stringent conditions to a nucleic acid molecule having the nucleotide sequence of SEQ ID Nos: 1, or 3, or its complement, and (c) a nucleic acid molecule that encodes a functional fragment of the polypeptide encoded by either (a) or (b). Preferably, the nucleic acid molecule is not JM2. Within related aspects, vectors (including expression vectors), and recombinant host cells are also provided, as well as proteins which are encoded by the above-noted nucleic acid molecules. Further, fusion proteins are also provided which combine at least a portion of the above-described nucleic acid molecules with the coding region of another protein. Also provided are oligonucleotide fragments (including probes and primers) which are based upon the above sequence. Such fragments are at least 8, 10, 12. 15, 20, or 25 nucleotides in length, and may extend up to 100, 200, 500, 1000, 1500, or, 2000 nucleotides in length.

Within other aspects methods of using the above noted expression vector for producing a $Fkh^{sf}$ protein (of any type) are provided, comprising the general steps of (a) culturing recombinant host cells that comprise the expression vector and that produce $Fkh^{sf}$ protein, and (b) isolating protein from the cultured recombinant host cells.

Also provided are antibodies and antibody fragments that specifically bind to $Fkh^{sf}$ proteins. Representative examples of such antibodies include both polyclonal and monoclonal antibodies (whether obtained from a murine hybridoma, or derived into human form). Representative examples of antibody fragments include $F(ab')_2$, $F(ab)_2$, Fab', Fab, Fv, sFv, and minimal recognition units or complementarity determining regions.

Within yet other aspects, methods are provided for detecting the presence of a $Fkh^{sf}$ nucleic acid sequence in a biological sample from a subject. comprising the steps of (a) contacting a $Fkh^{sf}$ specific nucleic acid probe under hybridizing conditions with either (i) test nucleic acid molecules isolated from said biological sample, or (ii) nucleic acid molecules synthesized from RNA molecules, wherein said probe recognizes at least a portion of nucleotide sequence of claim 1, and (b) detecting the formation of hybrids of said nucleic acid probe and (i) or (ii).

Within another related embodiment, methods are provided for detecting the presence of an Fkh$^{sf}$, or a mutant form thereof, in a biological sample, comprising the steps of: (a) contacting a biological sample with an anti-Fkh$^{sf}$ antibody or an antibody fragment, wherein said contacting is performed under conditions that allow the binding of said antibody or antibody fragment to said biological sample, and (b) detecting any of said bound antibody or bound antibody fragment.

Within other aspects of the invention, methods are provided for introducing Fkh$^{sf}$ nucleic acid molecules to an animal. comprising the step of administering a Fkh$^{sf}$ nucleic acid molecule as described herein to an animal (e.g., a human, monkey, dog, cat, rat, or, mouse. Within one embodiment, the nucleic acid molecule is contained within and expressed by a viral vector (e.g., a vector generated at least in part from a retrovirus, adenovirus, adeno-associated virus, herpes virus, or, alphavirus). Within another embodiment the nucleic acid molecule is expressed by, or contained within a plasmid vector. Such vectors may be administered either in vivo, or ex vivo (e.g., to hematopoietic cells such as T cells.

Within other embodiments, transgenic non-human animals are provided wherein the cells of the animal express a transgene that contains a sequence encoding Fkh$^{sf}$ protein.

These and other aspects of the present invention will become evident upon reference to the following detailed description and attached drawings. In addition. various references are set forth herein which describe in more detail certain procedures or compositions (e.g, plasmids, etc.), and are therefore incorporated by reference in their entirety.

BRIEF DESCRIPTION OF THEE DRAWINGS

FIG. 1 depicts a nucleotide sequence of mouse Fkh$^{sf}$ cDNA (Seqeunce I.D. No. 1); translation is predicted to initiate at position 259 and terminate at position 1546.

FIG. 2 depicts the amino acid sequence of mouse Fkh$^{sf}$ (Sequence I.D. No. 2).

FIG. 3 depicts a nucleotide sequence of 1735 bp corresponding to human FKH$^{sf}$ cDNA (Sequence I.D. No. 3; including a 1293 bp coding region); translation is predicted to initiate at position 55 and terminate at position 1348.

FIG. 4 depicts the sequence of a 431 amino acid human FKH$^{sf}$ protein (Sequence I.D. No. 4).

Figure 5:
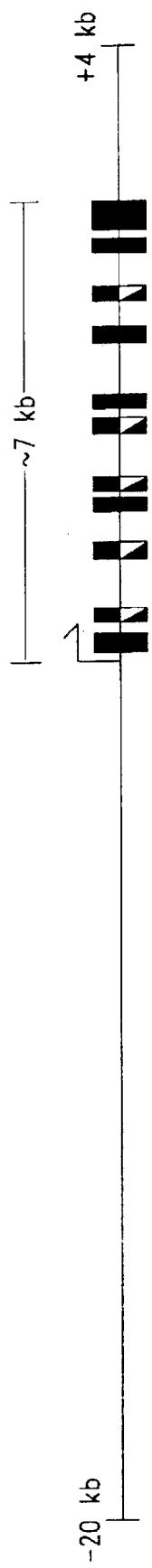

FIG. 5 diagrammatically depicts a vector for generation of FKH$^{sf}$ transgenic mice.

Figure 6:
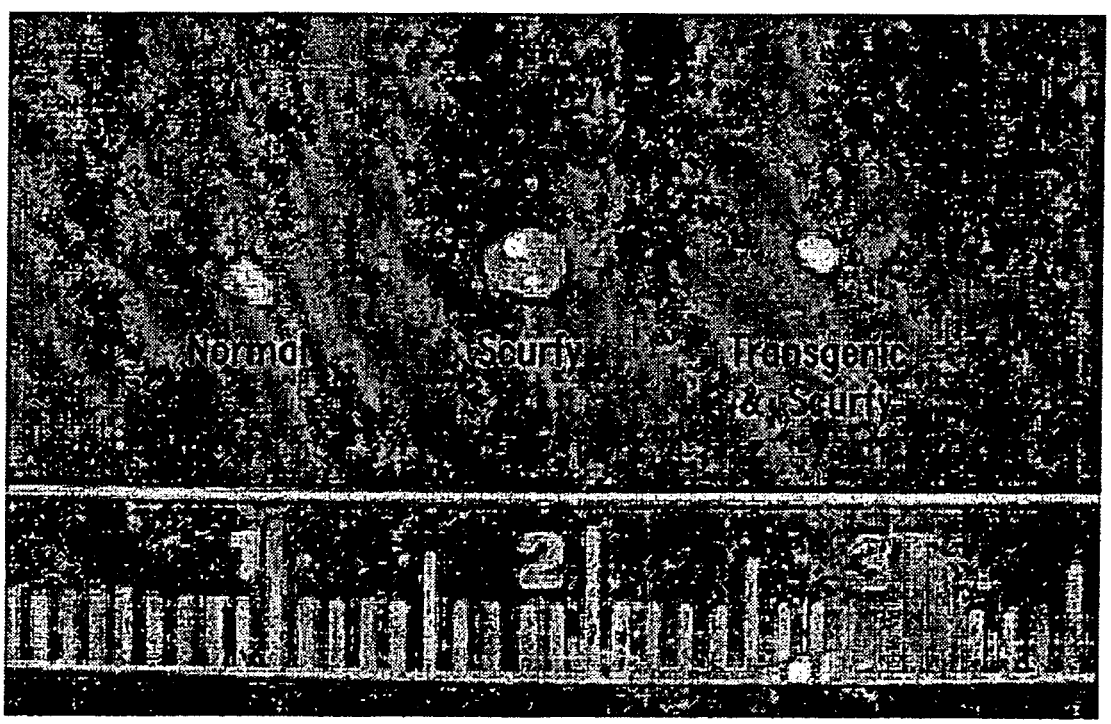

FIG. 6 is a photograph which demonstrates that the FKH$^{sf}$ transgene corrects the defect in scurfy animals.

FIG. 7 is a graph which shows that FKH$^{sf}$ tg mice have reduced lymph node cells, as compared to normal cells.

FIG. 8 is a graph which shows that FKH$^{sf}$ transgenic mice respond poorly to in vitro stimulation.

FIG. 9 is a comparison of FKH$^{sf}$ and JM2 cDNAs.

FIG. 10 compares homology in various regions of human FKH$^{sf}$ and murine Fkh$^{sf}$.

DETAILED DESCRIPTION OF THE INVENTION

Definitions

Prior to setting forth the Invention in detail, it may be helpful to an understanding thereof to set forth-definitions of certain terms and to list and to define the abbreviations that will be used hereinafter.

"Scurfy" refers to an inherited disease in mice which exhibit a severe lymphoproliferative disorder (see, e.g., Lyon et al., *Proc. Natl. Acad. Sci. USA* 87:2433, 1990). The responsible gene (mutant forms of which are responsible for the disease) is shown in Sequence I.D. Nos. 1 and 3.

"Molecule" should be understood to include proteins or peptides (e.g., antibodies, recombinant binding partners, peptides with a desired binding affinity), nucleic acids (e.g., DNA, RNA, chimeric nucleic acid molecules, and nucleic acid analogues such as PNA), and organic or inorganic compounds.

"Nucleic acid" or "nucleic acid molecule" refers to any of deoxyribonucleic acid (DNA). ribonucleic acid (RNA). oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover. the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate. phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

"Isolated nucleic acid molecule" is a nucleic acid, molecule that is not integrated in the genomic DNA of an organism. For example, a DNA molecule that encodes a gene that has been separated from the genomic DNA of a eukaryotic cell is an isolated DNA molecule. Another example of an isolated nucleic acid molecule is a chemically-synthesized nucleic acid molecule that is not integrated in the genome of an organism.

"Promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

"Vector" refers to an assembly which is capable of directing the expression of desired protein. The vector must include transcriptional promoter elements which are operably linked to the genes of interest. The vector may be composed of either deoxyribonucleic acids ("DNA"), ribonucleic acids ("RNA"), or a combination of the two (e.g, a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

"Isolated" in the case of proteins or polypeptides, refers to molecules which are present in the substantial absence of other biological macromolecules, and appear nominally as a single band on SDS-PAGE gel with coomassie blue staining. "Isolated" when referring to organic molecules means that the compounds are greater than 90% pure utilizing methods which are well known in the art (e.g. NMR, melting point).

"Cloning vector" refers to nucleic acid molecules, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

"Expression vector" refers to a nucleic acid molecule encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter.

"Recombinant host" refers to any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for $Fkh^{sf}$" or a "$Fkh^{sf}$ anti-sense oligonucleotide" is an oligonucleotide having a sequence (a) capable of forming a stable triplex with a portion of the gene, or (b) capable of forming a stable duplex with a portion of an mRNA transcript. Similarly, an "anti-sense oligonucleotide" specific for "$Fkh^{sf}$" or a "$Fkh^{sf}$ anti-sense oligonucleotide" is an oligonucleotide having a sequence (a) capable of forming a stable triplex with a portion of the $Fkh^{sf}$ gene, or (b) capable of forming a stable duplex with a portion of an mRNA transcript of the $Fkh^{sf}$ gene.

A "ribozymine" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

Abbreviations: YAC, yeast artificial chromosome; PCR, polymerase chain reaction; RT-PCR, PCR process in which RNA is first transcribed into DNA at the first step using reverse transcriptase (RT); cDNA, any DNA made by copying an RNA sequence into DNA form. As utilized herein "$Fkh^{sf}$" refers to the gene product of the $Fkh^{sf}$ gene (irrespective of whether the gene is obtained from humans, mammals, or any other warm-blooded animal). When capitalized "$FKH^{sf}$" the gene product (and gene) should be understood to be derived from humans.

As noted above, the present invention relates generally to pharmaceutical products and methods and, more specifically, to methods and compositions useful for diagnosing scurfy-related diseases, as well as methods for identifying compounds which can modulate the immune system.

Thus, as discussed in more detail below this discovery has led to the development of assays which may be utilized to select molecules which can act as agonists, or alternatively, antagonists of the immune system. Furthermore, such assays may be utilized to identify other genes and gene products which are likewise active in modulating the immune system.

Scurfy

Briefly, the present inventions are based upon the unexpected discovery that a mutation in the gene which encodes $Fkh^{sf}$ results in rare condition (scurfy) characterized by a progressive lymphocytic infiltration of the lymph nodes, spleen, liver and skin resulting in gross morphological symptoms which include splenomegaly, hepatomegaly, greatly enlarged lymph nodes, runting, exfoliative dermatitis, and thickened malformed ears (Godfrey et al., *Amer. J. Pathol.* 138:1379, 1991; Godfrey et al., *Proc. Natl. Acad. Sci. USA* 88:5528, 1991). This new member of the winged-helix family represents a novel component of the immune system.

Methods which were utilized to discover the gene responsible for scurfy are provided below in Example 1. Methods for cloning the gene responsible for murine scurfy, as well as the human ortholog, are provided below in Examples 2 and 3. Methods for confirmation of gene identity and correlation with gene function, as determined using transgenic mice, are also provided in the Examples.

Also provided by the present invention are methods for determining the presence of $Fkh^{sf}$ genes and gene products. Within one embodiment, such methods comprise the general steps of (a) contacting a $Fkh^{sf}$ specific nucleic acid probe under hybridizing conditions with either (i) test nucleic acid molecules isolated from the biological sample, or (ii) nucleic acid molecules synthesized from RNA molecules, wherein the probe recognizes at least a portion of an $Fkh^{sf}$ nucleotide sequence, and (b) detecting the formation of hybrids of said nucleic acid probe and (i) or (ii). A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and nucleic acid amplification utilizing Polymerase Chain Reaction ("PCR") (see U.S. Pat. Nos. 4,683.195. 4,683,202, and 4,800,159), reverse-transcriptase-PCR and CPT (see U.S. Pat. Nos. 4.876,187, and 5,011,769).

Alternatively, antibodies may be utilized to detect the presence of $Fkh^{sf}$ gene products. More specifically, within one embodiment methods are provided for detecting the presence of an Fkh$^{sf}$ peptide, or a mutant form thereof, in a biological sample, comprising the steps of (a) contacting a biological sample with an anti-Fkh$^{sf}$ antibody or an antibody fragment, wherein said contacting is performed under conditions that allow the binding of said antibody or antibody fragment to the biological sample, and (b) detecting any of the bound antibody or bound antibody fragment.

Such methods may be accomplished in a wide variety of assay formats including, for example, Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also *Antibodies: A Laboratory Manual*, supra).

Nucleic Acid Molecules. Proteins, and Methods of Producing Proteins

Although various FKH$^{sf}$ or Fkh$^{sf}$ proteins and nucleic acid molecules (or portions thereof) have been provided herein, it should be understood that within the context of the present invention, reference to one or more of these proteins should be understood to include proteins of a substantially similar activity. As used herein. proteins are deemed to be "substantially similar" if: (a) they are encoded by a nucleotide sequence which is derived from the coding region of a gene which encodes the protein (including, for example, portions of the sequence or allelic variations of the sequence); (b) the nucleotide sequence is capable of hybridization to nucleotide sequences of the present invention under moderate, high or very high stringency (see Sambrook et al., *Molecular Cloning: A Laboratory Manual,* 2nd ed., Cold Spring Harbor Laboratory Press, N.Y., 1989), or has at least 50%, 60%, 70%. 75%, 80%, 90%, 95%, or greater homology to the sequences disclosed herein, or, (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C. or the equivalent). For purpose of hybridization, nucleic acid molecules which encode the amino-terminal domain, zinc finger domain, middle domain, or forkhead domain (see Example 10) may be utilized.

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982).

Proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the proteins disclosed herein include conjugates of the proteins along with other proteins or polypeptides. This may be accomplished, for example. by the synthesis of N-terminal or C-terminal fusion proteins which may be added to facilitate purification or identification of proteins (see U.S. Pat. No. 4,851,341, see also, Hopp et al., *Bio/Technology* 6:1204, 1988.) Alternatively, fusion proteins (e.g., FKH or Fkh-luciferase or FKH or Fkh-GFP) may be constructed in order to assist in the identification, expression, and analysis of the protein.

Proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution. deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985. 12–19); Smith et al. (*Genetic Engineering: Principles and Methods,* Plenum Press, 1981); and Sambrook et al. (supra). Deletion or truncation derivatives of proteins (e.g., a soluble extracellular portion) may also be constructed by utilizing convenient restriction endonuclease sites adjacent to the desired deletion. Subsequent to restriction. overhangs may be filled in, and the DNA religated. Exemplary methods of making the alterations set forth above are disclosed by Sambrook et al. (*Molecular Cloning: A Laboratory Manual,* 2d Ed., Cold Spring Harbor Laboratory Press, 1989).

Mutations which are made in the nucleic acid molecules of the present invention preferably preserve the reading frame of the coding sequences. Furthermore. the mutations will preferably not create complementary regions that could hybridize to produce secondary mRNA structures. such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion. Mutations may be introduced for purpose of preserving or increasing activity of the protein, or, for decreasing or disabling the protein (e.g., mutant Fkh).

Nucleic acid molecules which encode proteins of the present invention may also be constructed utilizing techniques of PCR mutagenesis, chemical mutagenesis (Drinkwater and Klinedinst, *PNAS* 83:3402–3406, 1986), by forced nucleotide misincorporation (e.g., Liao and Wise *Gene* 88: 107–111, 1990), or by use of randomly mutagenized oligonucleotides (Horwitz et al., *Genome* 3:112–117, 1989).

The present invention also provides for the manipulation and expression of the above described genes by culturing host cells containing a vector capable of expressing the above-described genes. Such vectors or vector constructs include either synthetic or cDNA-derived nucleic acid molecules encoding the desired protein, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence. a transcriptional terminator, and a ribosomal binding sequence, including a translation initiation signal.

Nucleic acid molecules that encode any of the proteins described above may be readily expressed by a wide variety of prokaryotic and eukaryotic host cells, including bacterial, mammalian. yeast or other fungi, viral, insect, or plant cells. Methods for transforming or transfecting such cells to express foreign DNA are well known in the art (see, e.g., Itakura et al., U.S. Pat. No. 4,704,362: Hinnen et al. *Proc. Natl. Acad. Sci. USA* 75:1929–1933. 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4.766,075; and Sambrook et al. *Molecular Cloning: A Laboratory Manual,* 2nd ed., Cold Spring Harbor Laboratory Press, 1989; for plant cells see Czako and Marton, *Plant Physiol.* 104:1067–1071, 1994; and Paszkowski et al., *Biotech.* 24:387–392, 1992).

Bacterial host cells suitable for carrying out the present invention include *E. coli, B. subtilis, Salmonella typhimurium,* and various species within the genera *Pseudomonas, Streptomyces,* and *Staphylococcus,* as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20–77, 1983 and Vieira and Messing, *Gene* 19:259–268. 1982), and pNH8A, pNH16a, pNH18a, and Bluescript M13 (Stratagene, La Jolla Calif.).

Yeast and fungi host cells suitable for carrying out the present invention include, among others, *Saccharomyces pombe. Saccharomyces cerevisiae,* the genera *Pichia* or *Kluyveromyces* and various species of the genus *Aspergillus* (McKnight et al., U.S. Pat. No. 4,935,349). Suitable expression vectors for yeast and fungi include. among others. YCp50 (ATCC No. 37419) for yeast, and the amdS cloning vector pV3 (Turnbull, *Bio/Technology* 7:169. 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals,* Hollaender et al. (eds.), p. 355, Plenum, New York, 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors. the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (se e Itoh et al., *J. Bacteriology* 153:163. 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes a desired protein as described above. A wide variety of promoters may be utilized within the context of the present invention, including for example. promoters such as MoMLV LTR, RSV LTR, Friend MuLV LTR, adenoviral promoter (Ohno et al., *Science* 265:781–784, 1994), neomycin phosphotransferase promoter/enhancer, late parvovirus promoter (Koering et al., *Hum. Gene Therap.* 5:457–463. 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, human alphal-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281: BHK 570 cell line (deposited with the American Type Culture Collection under accession number CRL 10314)), CHO (ATCC No. CCL 61). HeLa (e.g. ATCC No. CCL 2), 293 (ATCC No. 1573; Graham et al., *J. Gen. Virol.* 36:59–72. 1977) and NS-1 cells. Other mammalian cell lines may be used within the present invention, including Rat Hep I (ATCC No. CRL 1600). Rat Hep II (ATCC No. CRL 1548). TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1). SP2/0-Ag14 (ATCC No. 1581), HIT-T15 (ATCC No. CRL 1777), Jurkat (ATCC No. Tib 152) and RINm 5AHT$_2$B (Orskov and Nielson, *FEBS* 229(1):175–178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981). MMTV LTR, RSV LTR, metallothionein-1, adenovirus E1a. Cellular promoters include the mouse metallothionein-1 promoter (Palmiter et al., U.S. Pat. No. 4,579,821), a mouse V$_K$ promoter (Bergman et al., *Proc. Natl. Acad. Sci. USA* 81:7041–7045, 1983; Grant et al., *Nucl. Acids Res.* 15:5496, 1987) and a mouse V$_H$ promoter (Loh et al., *Cell* 33:85–93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene. La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in molecular Biology,* John Wiley and Sons, Inc., NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs. such as neomycin, hygromycin, and methotrexate. Other selectable markers include fluorescent proteins such as GFP (green fluorescent protein) or BFP (blue fluorescent protein). The selectable marker may be an amplifiable selectable marker. Preferred amplifiable selectable markers are the DHFR gene and the neomycin resistance gene. Selectable markers are reviewed by Thilly (*Mammalian Cell Technology,* Butterworth Publishers, Stoneham, Mass., which is incorporated herein by reference).

Mammalian cells containing a suitable vector are allowed to grow for a period of time, typically 1–2 days. to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production. Cells may also be selected for transfection based on their expression of GFP by sorting for GFP-positive cells using a flow cytometer.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224,1990).

Numerous plant host cells known in the art can also be useful within the present invention, in light of the subject specification. For example, the use of *Agrobacterium rhizogenes* as vectors for expressing genes in plant cells has been reviewed by Sinkar et al. (*J. Biosci.* (*Bangalore*) 11:47–58, 1987).

Within related aspects of the present invention, proteins of the present invention, may be expressed in a transgenic animal whose germ cells and somatic cells contain a gene which encodes the desired protein and which is operably linked to a promoter effective for the expression of the gene. Alternatively, in a similar manner transgenic animals may be prepared that lack the desired gene (e.g., "knockout" mice). Such transgenics may be prepared n a variety non-human animals, including mice, rats, rabbits, sheep, dogs, goats and pigs (see Hammer et al., *Nature* 315:680–683, 1985, Palmiter et al., *Science* 222:809–814, 1983, Brinster et al., *Proc. Natl. Acad. Sci. USA* 82:4438–4442, 1985, Palmiter and Brinster, *Cell* 41:343–345, 1985, and U.S. Pat. Nos. 5,175, 383, 5,087,571, 4,736,866, 5,387,742, 5,347,075, 5,221,778, and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Animals which produce mutant forms of $Fkh^{sf}$ other than the naturally occurring scurfy mutant ("sf"), or in genetic backgrounds different from the naturally occurring mutant, may be readily produced given the disclosure provided herein.

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an antiprotein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

Assays for Selecting Molecules which Modulate the Inmmune System

As noted above, the present invention provides methods for selecting and/or isolating molecules which are capable of modulating the immune system. Representative examples of suitable assays include the yeast and mammalian 2-hybrid systems (e.g., Dang et al., *Mol. Cell. Biol.* 11:954, 1991 Fearon et al., *Proc. Natl. Acad. Sci. USA* 89:7958, 1992), DNA binding assays, antisense assays, traditional protein binding assays (e.g., utilizing $^{125}I$ or time-resolved fluorescence), immunopreceipitation coupled with gel electrophoresis and direct protein sequencing, transcriptional analysis of $Fkh^{sf}$ regulated genes, cytokine production and proliferation assays.

For example, within one embodiment proteins that directly interact with $Fkh^{sf}$ can be detected by an assay such as a yeast 2-hybrid binding system (see, e.g., U.S. Pat. Nos. 5,283,173, 5,468,614, 5,610,015, and 5,667,973). Briefly, in a two-hybrid system, a fusion of a DNA-binding domain-$Fkh^{sf}$ protein (e.g., GAL4-$Fkh^{sf}$ fusion) is constructed and transfected into a cell containing a GAL4 binding site linked to a selectable marker gene. The whole $Fkh^{sf}$ protein or subregions of $Fkh^{sf}$ may be used. A library of cDNAs fused to the GAL4 activation domain is also constructed and co-transfected. When the cDNA in the cDNA-GAL4 activation domain fusion encodes a protein that interacts with $Fkh^{sf}$, the selectable marker is expressed. Cells containing the cDNA are then grown, the construct isolated and characterized. Other assays may also be used to identify interacting proteins. Such assays include ELISA, Western blotting, co-immunoprecipitations, in vitro transcription/translation analysis and the like.

Within another aspect of the present invention, methods are provided for determining whether a selected molecule is capable of modulating the immune system comprising the steps of (a) exposing a selected candidate molecule to cells which express $Fkh^{sf}$, or, mutant $Fkh^{sf}$, and (b) determining whether the molecule modulates the activity of $Fkh^{sf}$, and thereby determining whether said molecule can modulate the immune system. Cells for such tests may derive from (a) normal lymphocytes, (b) cell lines engineered to overexpress the $FKH^{sf}$ (or $Fkh^{sf}$) protein (or mutant forms thereof) or (c) transgenic animals engineered to express said protein. Cells from such transgenic mice are characterized, in part, by a hyporesponsive state including diminished cell number and a decreased responsiveness to various stimuli (e.g., Example 8).

It should be noted that while the methods recited herein may refer to the analysis of an individual test molecule, that the present invention should not be so limited. In particular, the selected molecule may be contained within a mixture of compounds. Hence, the recited methods may further comprise the step of isolating the desired molecule. Furthermore, it should be understood that candidate molecules can be assessed for their ability to modulate the immune system by a number of parameters, including for example, T-cell proliferation, cytokine production, and the like.

Candidate Molecules

A wide variety of molecules may be assayed for their ability to modulate the immune system. Representative examples which are discussed in more detail below include organic molecules, proteins or peptides, and nucleic acid molecules.

1. Organic Molecules

Numerous organic molecules may be assayed for their ability to modulate the immune system. For example, within one embodiment of the invention suitable organic molecules may be selected either from a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209: Lerner. R. et al., "Encoded combinatorial chemical libraries." WO 93/20242: Pavia. M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips. G. B. and G. P. Wei, "Solid-phase Synthesis of Benzimidazoles," *Tet. Letters* 37:4887–90, 1996; Ruhland, B. et al., "Solid-supported Combinatorial Synthesis of Structurally Diverse β-Lactams," *J. Amer. Chem. Soc.* 111:253–4, 1996; Look, G. C. et al., "The Indentification of Cyclooxygenase-1 Inhibitors from 4-Thiazolidinone Combinatorial Libraries," *Bioorg and Med. Chem. Letters* 6:707–12, 1996.

2. Proteins and Peptides

A wide range of proteins and peptides make likewise be utilized as candidate molecules for modulating the immune system.

a. Combinatorial Peptide Libraries

Peptide molecules which modulate the immune system may be obtained through the screening of combinatorial peptide libraries. Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

b. Antibodies

Antibodies which modulate the immune system may readily be prepared given the disclosure provided herein. Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). As discussed above, antibodies are understood to be specific against Fkh$^{sf}$ if they bind with a K$_a$ of greater than or equal to $10^7$-M$^{-1}$, preferably greater than of equal to $10^8$-M$^{-1}$. The affinity of a monoclonal antibody or binding partner, as well as inhibition of binding can be readily determined by one of ordinary skill in the art (see Scatchard, *Ann. N.Y. Acad. Sci.* 51:660–672, 1949).

Briefly, polyclonal antibodies may be readily generated by one of ordinary skill in the art from a variety of warm-blooded animals such as horses, cows, various fowl, rabbits, mice, or rats. Typically, Fkh$^{sf}$, or a unique peptide thereof of 13–20 amino acids (preferably conjugated to keyhole limpet hemocyanin by cross-linking with glutaraldehyde) is utilized to immunize the animal through intraperitoneal, intramuscular, intraocular, or subcutaneous injections, in conjunction with an adjuvant such as Freund's complete or incomplete adjuvant. Following several booster immunizations, samples of serum are collected and tested for reactivity to the protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4.902,614, 4,543,439, and 4,411,993 which are incorporated herein by reference; see also *Monoclonal Antibodies, Hybridomas: A New Dimension in Biological Analyses,* Plenum Press, Kennett, McKearn, and Bechtol (eds.), 1980, and *Antibodies: A Laboratory Manual,* Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, August 1989: see also Michelle Alting-Mees et al., "Monoclonal Antibody Expression Libraries: A Rapid Alternative to Hybridomas." *Strategies in Molecular Biology* 3:1–9. January 1990).

A wide variety of assays may be utilized to determine the presence of antibodies which are reactive against the Fkh$^{sf}$ (or the mutant forms of Fkh$^{sf}$ described herein), including for example countercurrent immuno-electrophoresis, radioimmunoassays, radioimmunoprecipitations, enzyme-linked immuno-sorbent assays (ELISA), dot blot assays, western blots, immunoprecipitation, Inhibition or Competition Assays, and sandwich assays (see U.S. Pat. Nos. 4,376, 110 and 4,486,530; see also *Antibodies: A Laboratory Manual,* Harlow and Lane (eds.), Cold Spring Harbor Laboratory Press, 1988).

Once suitable antibodies have been obtained. they may be isolated or purified by many techniques well known to those of ordinary skill in the art (see *Antibodies: A Laboratory Manual,* Harlow and Lane (eds.), Cold Spring Harbor Laboratory Press, 1988). Suitable techniques include peptide or protein affinity columns, HPLC or RP-HPLC, purification on protein A or protein G columns. or any combination of these techniques.

Antibodies of the present invention may be utilized not only for modulating the immune system, but for diagnostic tests (e.g., to determine the presence of an FKH$^{sf}$ or Fkh$^{sf}$ protein or peptide), for therapeutic purpose, or for purification of proteins.

c. Mutant Fkh$^{sf}$

As described herein and below in the Examples, altered versions of Fkh$^{sf}$ may be utilized to inhibit the normal activity of Fkh$^{sf}$ thereby modulating the immune system (see generally, nucleic acid molecules and proteins above).

Further mutant or altered forms of FKH$^{sf}$ or Fkh$^{sf}$ may be utilized for a wide variety of in vitro assays (e.g., in order to examine the affect of such proteins in various models), or, for the development of antibodies.

3. Nucleic Acid Molecules

Within other aspects of the invention, nucleic acid molecules are provided which are capable of modulating the immune system. For example, within one embodiment antisense oligonucleotide molecules are provided which specifically inhibit expression of $FKH^{sf}$ or $Fkh^{sf}$ nucleic acid sequences, or, of mutant $FKH^{sf}$ or $Fkh^{sf}$ (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012, 1993; WO 95/10607; U.S. Pat. No. 5,359, 051; WO 92/06693; and EP-A2-612844). Briefly, such molecules are constructed such that they are complementary to, and able to form Watson-Crick base pairs with, a region of transcribed $Fkh^{sf}$ mRNA sequence. The resultant double-stranded nucleic acid interferes with subsequent processing of the mRNA, thereby preventing protein synthesis.

Within other aspects of the invention, ribozymes are provided which are capable of inhibiting $FKH^{sf}$ or $Fkh^{sf}$ or mutant forms FKHh$^{sf}$ or Fkh$^{sf}$. As used herein, "ribozymes" are intended to include RNA molecules that contain antisense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211–220. 1987; Haseloff and Gerlach. *Nature* 328:596–600, 1988; Walbot and Bruening, *Nature* 334:196, 1988; Haseloff and Gerlach. *Nature* 334:585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates) or chimerics thereof (e.g., DNA/RNA/ RNA).

4. Labels

Fkh$^{sf}$ or Fkh$^{sf}$. (as well as mutant forms thereof), or, any of the candidate molecules described above and below, may be labeled with a variety of compounds. including for example, fluorescent molecules, toxins, and radionuclides. Representative examples of fluorescent molecules include fluorescein, *Phycobili* proteins, such as phycoerythrin, rhodamine, Texas red and luciferase. Representative examples of toxins include ricin, abrin diphtheria toxin, cholera toxin, gelonin, pokeweed antiviral protein, tritin, *Shigella* toxin, and *Pseudomonas* exotoxin A. Representative examples of radionuclides include Cu-64, Ga-67, Ga-68, Zr-89. Ru-97, Tc-99m, Rh-105. Pd-109, In-111, I-123, I-125, I-131, Re-186. Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate. U.S. Pat. No. 4,744,981; Antibody Conjugate, U.S. Pat. No. 5,106, 951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1–32, 1988).

Pharmaceutical Compositions

As noted above, the present invention also provides a variety of pharmaceutical compositions, comprising one of the above-described molecules which modulates the immune system, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, the pharmaceutical composition (or, 'medicament') is provided in sterile, pyrogen-free form.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treatment

The present invention also provides methods for modulating the immune system. Through use of the molecules described herein which modulate the immune system, a wide variety of conditions in warm blooded animals may be readily treated or prevented. Examples of warm-blooded animals that may be treated include both vertebrates and mammals, including for example humans, horses, cows, pigs. sheep, dogs, cats, rats and mice. Such methods may have therapeutic value in patients with altered immune systems. This would include such patients as those undergoing chemotherapy of those with various immunodeficiency syndromes. as well as patients with a T cell mediated autoimmune disease. Therapeutic value may also be recognized from utility as a vaccine adjuvant.

Therapeutic molecules. depending on the type of molecule. may be administered via a variety of routes in a variety of formulations. For example. within one embodiment organic molecules may be delivered by oral or nasal routes. or by injection (e.g., intramuscularly. intravenously, and the like).

Within one aspect. methods are provided for modulating the immune system, comprising the step of introducing into lymphoid cells a vector which directs the expression of a molecule which modulates the immune system, and administering the vector containing cells to a warm-blooded animal. Within other related embodiments, the vector may be directly administered to a desired target location (e.g., the bone marrow).

A wide variety of vectors may be utilized for such therapeutic purposes. including both viral and non-viral vectors. Representative examples of suitable viral vectors include herpes viral vectors (e.g., U.S. Pat. No. 5,288,641), adenoviral vectors (e.g., WO 94/26914, WO 93/9191 WO 99/20778; WO 99/20773; WO 99120779; Kolls et al., *PNAS* 91(1):215–219. 1994; Kass-Eisler et al., *PNAS* 90(24): 11498–502, 1993; Guzman et al., *Circulation* 88(6):283 848, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2): 130–134, 1993; Jaffe et al., *Nat. Genet.* 1(5):372–378, 1992: and Levrero et al., *Gene* 101(2):195–202, 1991), adeno-associated viral vectors (WO 95/13365; Flotte et al., *PNAS* 90(22):10613–10617, 1993), baculovirus vectors, parvovirus vectors (Koering et al., *Hum. Gene Therap.* 5:457463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218). Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Within other embodiments of the invention, nucleic acid molecules which encode a molecule which modulates the immune system (e g., a mutant $Fkh^{sf}$, or, an antisense or ribozyme molecule which cleaves $Fkh^{sf}$) may be administered by a variety of alternative techniques, including for example administration of asialoosomucoid (ASOR) conjugated with poly-L-lysine DNA complexes (Cristano et al., *PNAS* 92122–92126, 1993), DNA linked to killed adenovirus (Curiel et al., *Hum. Gene Ther.* 3(2):147–154, 1992), cytofectin-mediated introduction (DMRIE-DOPE. Vical, Calif.), direct DNA injection (Acsadi et al., *Nature* 352:815–818, 1991); DNA ligand (Wu et al., J. of Biol. Chem. 264:16985–16987, 1989); lipofection (Felgner et al., *Proc. Natl. Acad. Sci. USA* 84:7413–7417, 1989); liposomes (Pickering et al., *Circ.* 89(1):13–21, 1994; and Wang et al., *PNAS* 84:7851–7855, 1987); microprojectile bombardment (Williams et al., *PNAS* 88:2726–2730, 1991); and direct delivery of nucleic acids which encode the protein itself either alone (Vile and Hart, *Cancer Res.* 53: 3860–3864, 1993), or utilizing PEG-nucleic acid complexes.

Representative examples of molecules which may be expressed by the vectors of present invention include ribozymes and antisense molecules, each of which are discussed in more detail above.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The following examples are offered by way of illustration, and not by way of limitation.

EXAMPLES

Example 1

Identification of the Gene Responsible for the Scurfy Mutant

A. Cloning of a Scurfy Gene

The original scurfy mutation arose spontaneously in the partially inbred MR stock at Oak Ridge National Laboratory (ORNL) in 1949. Backcross analysis was used to fine map the peri-centromeric region of the X chromosome containing the mouse Scurfy mutation. A physical map covering the same region was generated concurrently through the isolation of overlapping yeast and bacterial artificial chromosomes (YACs and BACs). Once the candidate region was narrowed down to ~500 kilobase pairs (kb). large-scale DNA sequencing was performed on 4 overlapping BAC clones. All the transcription units in this 500 kb region were identified through a combination of sequence database searching and the application of computer exon prediction programs. Candidate genes were then screened for Scurfy-specific mutations by comparing the sequences of cDNAs obtained by the Reverse Transcription-Polymerase Chain Reaction (RT-PCR) procedure from normal and Scurfy-derived RNA samples. In one gene, referred to here as $Fkh^{sf}$, a two base pair (bp) insertion was found in the coding region of the Scurfy cDNA, relative to the normal cDNA. The insertion was confirmed by comparing the DNA sequences of PCR products derived from the genomic DNA of several mouse strains, including the Scurfy mutant. Again, the two bp insertion was found only in the Scurfy sample, establishing this as the probable cause of the Scurfy defect.

The mouse $Fkh^{sf}$ gene is contained within the BAC clone 8C22, and has been completely sequenced. It spans ~14 kb and contains 11 coding exons. The locations of exon breaks were initially identified by computer analysis of the genomic DNA sequence, using the GenScan exon prediction program; exon locations were then confirmed by direct comparison of cDNA sequences derived from normal mouse tissues to the genomic sequence.

The length of cDNA obtained is 2160 bp; the coding region spans 1287 bp of that, encoding a protein of 429 amino acids. FIG. 1 shows the nucleotide sequence of the mouse $Fkh^{sf}$ cDNA; translation is predicted to initiate at position 259 and terminate at position 1546. FIG. 2 shows the amino acid sequence of mouse $Fkh^{sf}$.

b. Generation of $Fkh^{sf}$ Transgenic Mice.

The identity of the $Fkh^{sf}$ gene as the true cause of the Scurfy phenotype was confirmed in transgenic mice. Briefly, a 30 kb fragment of the normal genomic DNA, including the ~7 kb coding region of the $Fkh^{sf}$ gene, as well as ~20 kb of upstream flanking sequences and ~4 kb of downstream sequences (FIG. 5) was microinjected into normal mouse one-cell embryos. Five individual founder animals were generated, each with distinct integrations. and a male animal from each transgenic line was crossed to a female sf carriers. Male offspring carrying both the transgene (normal $Fkh^{sf}$) and sf mutation (mutant $Fkh^{sf}$ were analyzed.

Analysis consisted of examination of animals for runting, scaly skin, fur abnormalities and other hallmarks of the scurry phenotype. In addition, lymphoid tissues (thymus, spleen and nodes) were harvested and their size and cell number examined and compared to both normal animals as well as scurfy mice. For all five transgenic lines, male sf progeny that carried the transgene were normal in size and weight and appeared healthy in all respects. Lymph node size in these transgenic mice was similar to (or smaller than) that of normal animals (FIG. 6) and there was no sign of activated T cells. These parameters are extremely different from sf mice and indicate that addition of the normal $Fkh^{sf}$ gene can overcome the defect found in scurfy mice. thus confirming that the mutation in the $Fkh^{sf}$ gene is the cause of Scurfy disease.

Example 2

Generation of $Fkh^{sf}$ cDNA

A complementary DNA (cDNA) encoding the complete mouse $Fkh^{sf}$ protein may be obtained by a reverse-transcriptase polymerase chain reaction (RT-PCR) procedure. More specifically, first-strand cDNA is generated by oligo dT priming 5 ug of total RNA from a suitable source (eg., mouse spleen) and extending with reverse transcriptase under standard conditions (eg., Gibco/BRL SuperScript kit). An aliquot of the first-strand cDNA is then subjected to 35 cycles of PCR (94° C. for 30 sec, 63° C. for 30 sec, 72° C. for 2 min) in the presence of the forward and reverse primers (Forward primer: GCAGATCTCC TGACTCTGCC TTC (SEQ ID NO:5); Reverse primer: GCAGATCTGA CAAGCTGTGT CTG) (SEQ ID NQ:6) (0.2 mM final concentration), 60 mM Tris-HCl, 15 mM ammonium sulfate, 1.5 mM magnesium chloride, 0.2 mM each dNTP and 1 unit of Taq polymerase.

Example 3

Generation of the Human Ortholog to Murine FKH$^{sf}$

A human FKF$^{sf}$ cDNA encoding the complete FKH$^{sf}$ protein may be obtained by essentially the same procedure as described in Example 2. In particular, starting with total spleen RNA, and utilizing the following oligonucleotide primers (Forward primer: AGCCTGCCCT TGGACAAGGA C (SEQ ID NO:7); Reverse primer: GCAAGACAGT GGAAACCTCA C) (SEQ ID NO:8), and the same PCR conditions outlined above, except with a 60° C. annealing temperature.

FIG. 3 shows the nucleotide sequence of the 1869 bp cDNA obtained to date (including an 1293 bp coding region); translation is predicted to initiate at position 189 and terminate at position 1482. FIG. 4 shows the sequence of the 431 amino acid human FKH$^{sf}$ protein. Comparison of the predicted coding region of the human gene to the mouse cDNA sequence reveals nearly identical exon structure and 86.1% amino acid sequence identity across the entire protein.

Example 4

Methods for Detecting Scurfy Mutations

As noted above, the Scurfy mutation was originally discovered by directly sequencing cDNAs derived by RT-PCR of sf and normal mouse RNA samples, and confirmed by sequencing the same region from genomic DNA. The nature of the mutation (i.e., a 2 bp insertion) lends itself to a number of different mutation detection assays. The first is based on differential hybridization of oligonucleotide probes. Such a hybridization-based assay could allow quantitative analysis of allele-specific expression.

As an example, a 360 bp DNA fragment is amplified from 1$^{st}$ strand cDNA using the following oligos:

```
DMO5985 (forward):  CTACCCACTGCTGGCAAATG     (ntd. 825–844 of FIG. 1)    (SEQ ID NO:9)

DMO6724 (reverse):  GAAGGAACTATTGCCATGGCTTC  (ntd 1221–1199)             (SEQ ID NO:10)
```

The PCR products are run on an 1.8% agarose gel, transferred to nylon membrane and probed with end-labeled oligonucleotides that are complementary to the region corresponding to the site of the Scurfy-specific 2 bp insertion. Two separate hybridization reactions are performed to detect the normal and Scurfy PCR products, using the oligonucleotides below (the site of the 2 bp insertion is shown in bold):

```
                                                      (SEQ ID NO:11)
Normal:  ATGCAGCAAGAGCTCTTGTCCATTGAGG
DMO7439

(SEQ ID NO:12)
Scurfy:  GCAGCAAGAGCTCTTTTGTCCATTGAGG
DMO6919
```

The Scurfy mutation can also be detected by a cold Single-Strand Conformation Polymorphism (cSSCP) assay. In this assay, the same PCR products described above are run on 20% acrylamide (TBE) gels after strand denaturation. The Scurfy insertion causes a shift in strand mobility, relative to the normal sequence, and the separate strands are detected after staining with ethidium bromide.

Example 5

FKH$^{sf}$ Gene Expression

Semi-quantitative RT-PCR has been used to analyze the pattern of mouse and human Fkh$^{sf}$ gene expression in a wide variety of tissues and cell lines. Levels of expression are normalized to the ubiquitously expressed DAD-1 gene. In short, the Fkh$^{sf}$ gene is expressed. albeit at very low levels, in nearly every tissue examined thus far, including thymus, spleen, sorted CD4+ and CD4–CD8–T-lymphocytes, as well as kidney, brain, and various mouse and human T-cell lines and human tumors. Absence of expression, however, was noted in freshly sorted mouse B-cells.

As expected, no differences in level of expression were observed in normal vs. Scurfy tissues in the RT-PCR assays.

Example 6

In Vitro Expression of Fkh$^{sf}$

Full-length mouse and human Fkh$^{sf}$ cDNAs, as well as various sub-regions of the cDNAs are cloned into vectors which allow expression in mammalian cells (such as the human Jurkat T-cell line), E. coli or yeast. The E. coli or yeast systems can be used for production of protein for the purpose of raising Fkh$^{sf}$-specific antibodies (see below).

Example 7

Generation of Anti-Fkh$^{sf}$ Antibodies

Protein expressed from vectors described in example 6 are used to immunize appropriate animals for the production of FKH$^{sf}$ specific antibodies. Either full length or truncated proteins can be used for this purpose. Protein can be obtained, for example, from bacteria such as E. coli, insect cells or mammalian cells. Animal species can include mouse, rabbit, guinea pig, chicken or other. Rabbit antisera specific for FKH$^{sf}$ has been generated, as determined by biochemical characterization (immunoprecipitation and western blotting).

Example 8

Assay for Function of an FKH$^{sf}$ Gene

Since loss of function of the FKH$^{sf}$ protein results in the phenotype observed in scurfy animals (wasting hyperactive immune responsiveness and death), assays are described for assessing excessive expression of the FKH$^{sf}$ protein. Transgenic animals (described in Example 1) are examined for their state of immune competence, using several different parameters. Animals are examined for the number of lymphoid cells present in lymph nodes and thymus (FIG. 7) as well as the responsiveness of T cells to in vitro stimulation (FIG. 8).

Scurfy mutant animals have roughly twice as many cells in their lymph nodes as normal animals, whereas mice which express excess levels of the normal FKH$^{sf}$ protein contain roughly one-third as many cells (FIG. 7). Further. the number of thymocytes is normal (FIG. 7) as is their cell surface phenotype as assessed by flow cytometry using standard antisera (not shown), indicating that there is no developmental defect associated with excess FKH$^{sf}$ protein.

Normal, scurfy and transgenic animals are further examined for their proliferative responses to T cell stimulation. CD4+ T cells are reacted with antibodies to CD3 and CD28 and their proliferative response measured using radioactive thymidine incorporation. Whereas only scurfy cells divide in the absence of stimulation, normal cells respond well following stimulation. FKH$^{sf}$ transgenic cells also respond to stimulation, however the response is significantly less than that of normal cells (FIG. 8). This indicates that CD4+ T cells that express excess FKH$^{sf}$ have a diminished capacity to respond to stimuli.

Example 9

Human FKH$^{sf}$ cDNA Sequence is Related to JM2

A modified version of the human FKH$^{sf}$ cDNA sequence exists in the GenBank public sequence database. This sequence is called JM2 (GenBank acc. # AJ005891), and is the result of the application of exon prediction programs to the genomic sequence containing the FKH$^{sf}$ gene (Strom, T. M. et al., unpublished—see GenBank acc. # AJ005891). In contrast, the structure of the FKH$^{sf}$ cDNA was determined experimentally. The GAP program of the Genetics Computer Group (GCG; Madison, USA) Wisconsin sequence analysis package was used to compare the two sequences, and the differences are illustrated in FIG. 9. The 5' ends of the two sequences differ in their location within the context of the genomic DNA sequence, the second coding exon of FKH$^{sf}$ is omitted from JM2, and the last intron of the FKH$^{sf}$ gene is unspliced in the JM2 sequence. These differences result in a JM2 protein with a shorter amino-terminal domain, relative to FKH$^{sf}$, and a large insertion within the forkhead domain (see below) at the carboxy-terminus.

Example 10

The FKH$^{sf}$ Protein is Conserved Across Species

The FKH$^{sf}$ protein can be divided into sub-regions, based on sequence motifs that may indicate functional domains. The two principal motifs in FKH$^{sf}$ are the single zinc finger (ZNF) of the $C_2H_2$ class in the middle portion of the protein, and the forkhead, or winged-helix domain at the extreme carboxy-terminus of the protein. For the purposes of characterizing the degree of homology between FKH$^{sf}$ and other proteins, we have split the protein up into four regions:

| | |
|---|---|
| Amino-terminal domain: | residues 1–197 of FIG. 2 |
| | residues 1–198 of FIG. 4 |
| Zinc finger domain: | residues 198–221 of FIG. 2 |
| | residues 199–222 of FIG. 4 |
| Middle domain: | residues 222–336 of FIG. 2 |
| | residues 223–336 of FIG. 4 |
| Forkhead domain: | residues 337–429 of FIG. 2 |
| | residues 337–431 of FIG. 4 |

Using the Multiple Sequence Alignment program from the DNAStar sequence analysis package, the Lipman-Pearson algorithm was employed to determine the degree of similarity between the human FKH$^{sf}$ and mouse Fkh$^{sf}$ proteins across these four domains. The results are shown in FIG. 10. The similarity indices ranged from 82.8% to 96.4%, indicating that this protein is very highly conserved across species.

Example 11

Identification of Novel FKH$^{SF}$-Related Genes

The unique features of the FKH$^{sf}$ gene sequence may be used to identify other novel genes (and proteins) which fall into the same sub-class of forkhead-containing molecules. The FKH$^{sf}$ protein is unique in its having a single zinc finger domain amino-terminal to the forkhead domain as well as in the extreme carboxy-terminal position of the forkhead domain. A degenerate PCR approach may be taken to isolate novel genes containing a zinc finger sequence upstream of a forkhead domain. By way of example, the following degenerate primers were synthesized (positions of degeneracy are indicated by parentheses, and "I" indicates the nucleoside inosine):

```
Forward primer:   CA(TC)GGIGA(GA)TG(CT)AA(GA)TGG          (SEQ ID NO:13)

Reverse primer:   (GA)AACCA(GA)TT(AG)TA(AGT)AT(CT)TC(GA)TT (SEQ ID NO:14)
```

The forward primer corresponds to a region within the zinc finger sequence and the reverse primer corresponds to a region in the middle of the forkhead domain. These primers were used to amplify first-strand cDNA produced as in Example 2 from a variety of human tissues (including liver, spleen, brain, lung, kidney, etc.). The following PCR conditions were used: forward and reverse primers at 0.2 mM final concentration, 60 mM Tris-HCl, 15 mM ammonium sulfate, 1.5 mM magnesium chloride, 0.2 mM each dNTP and 1 unit of Taq polymerase, subjected to 35 cycles (94° C. for 30 sec, 50° C. for 30 sec, 72° C. for 2 min). PCR products were visualized on a 1.8% agarose gel (run in 1×TAE) and sub-cloned into the TA cloning vector (Invitrogen, Carlsbad. Calif.); individual clones were sequenced and used for further characterization of full-length cDNAs.

Alternatively, the unique regions of the FKH$^{sf}$ gene (i.e., the "Amino-terminal" and "Middle" domains) may be used to screen cDNA libraries by hybridization. cDNA libraries, derived from a variety of human and/or mouse tissues, and propagated in lambda phage vectors (eg., lambda gtl1) were plated on agarose, plaques were transferred to nylon membranes and probed with fragments derived from the unique regions of the FKH$^{sf}$ gene. Under high stringency conditions (eg. hybridization in 5×SSPE, 5×Denhardt's solution, 0.5% SDS at 65° C., washed in 0.1×SSPE, 0.1% SDS at 65C) only very closely related sequences are expected to hybridize (i.e., 90–100% homologous). Under lower stringency, such as hybridization and washing at 45°–55° C. in the same buffer as above, genes that are related to FKH$^{sf}$ (65–90% homologous) may be identified. Based on results obtained from searching public databases with the unique sequences of FKH$^{sf}$ any genes identified through low- to mid-stringency hybridization experiments are expected to represent novel members of a "FKH$^{sf}$ family".

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated nucleic acid molecule comprising nucleotides 259 to 1548 of the polynucleotide sequence as provided in SEQ ID NO:1 or the complement thereof.

2. A vector comprising the nucleic acid molecule of claim 1.

3. A host cell transformed or transfected with the vector of claim 2.

4. An isolated nucleic acid molecule comprising nucleotides 189 to 1484 of the polynucleotide sequence as provided in SEQ ID NO:3 or the complement thereof.

5. A vector comprising the nucleic acid molecule of claim 4.

6. A host cell transformed or transfected with the vector of claim 5.

* * * * *

SEQUENCE LISTING

<160> NUMBER OF SEQ ID NOS: 14

<210> SEQ ID NO 1
<211> LENGTH: 2160
<212> TYPE: DNA
<213> ORGANISM: Mus musculus

<400> SEQUENCE: 1

```
gctgatcccc ctctagcagt ccacttcacc aaggtgagcg agtgtccctg ctctccccca      60
ccagacacag ctctgctggc gaaagtggca gagaggtatt gagggtgggt gtcaggagcc     120
caccagtaca gctggaaaca cccagccact ccagctcccg gcaacttctc ctgactctgc     180
cttcagacga gacttggaag acagtcacat ctcagcagct cctctgccgt tatccagcct     240
gcctctgaca agaacccaat gcccaaccct aggccagcca agcctatggc tccttccttg     300
gcccttggcc catccccagg agtcttgcca agctggaaga ctgcacccaa gggctcagaa     360
cttctaggga ccagggctc tggggaccc ttccaaggtc gggacctgcg aagtgggggcc     420 cacacctctt cttccttgaa cccctgcca ccatcccagc tgcagctgcc tacagtgccc     480
ctagtcatgt tggcaccgtc tggggccga ctaggtccct cacccacct acaggccctt     540 ctccaggaca gaccacactt catgcatcag ctctccactg tggatgccca tgcccagacc     600
cctgtgctcc aagtgcgtcc actggacaac ccagccatga tcagcctccc accaccttct     660
gctgccactg gggtcttctc cctcaaggcc cggcctggcc tgccacctgg gatcaatgtg     720
gccagtctgg aatgggtgtc cagggagcca gctctactct gcaccttccc acgctcgggt     780
acacccagga agacagcaa ccttttggct gcaccccaag gatcctaccc actgctggca     840
aatggagtct gcaagtggcc tggttgtgag aaggtcttcg aggagccaga gagtttctc     900 aagcactgcc aagcagatca tctcctggat gagaaaggca aggcccagtg cctcctccag     960
agagaagtgg tgcagtctct ggagcagcag ctggagctgg aaaaggagaa gctgggagct    1020
atgcaggccc acctggctgg gaagatggcg ctggccaagg ctccatctgt ggcctcaatg    1080
gacaagagct cttgctgcat cgtagccacc agtactcagg gcagtgtgct cccggcctgg    1140
tctgctcctc gggaggctcc agacggcggc ctgtttgcag tgcggaggca cctctgggga    1200
agccatggca atagttcctt cccagagttc ttccacaaca tggactactt caagtaccac    1260
aatatgcgac cccctttcac ctatgccacc cttatccgat gggccatcct ggaagccccg    1320
gagaggcaga ggacactcaa tgaaatctac cattggttta ctcgcatgtt cgcctacttc    1380
agaaaccacc ccgccacctg gaagaatgcc atccgccaca acctgagcct gcacaagtgc    1440
tttgtgcgag tggagagcga aagggagca gtgtggaccg tagatgaatt tgagtttcgc    1500
aagaagagga gccaacgccc caacaagtgc tccaatccct gcccttgacc tcaaaaccaa    1560
gaaaaggtgg gcgggggagg gggccaaaac catgagactg aggctgtggg ggcaaggagg    1620
```

-continued

```
caagtcctac gtgtacctat ggaaaccggg cgatgatgtg cctgctatca gggcctctgc   1680
tccctatcta gctgccctcc tagatcatat catctgcctt acagctgaga ggggtgccaa   1740
tcccagccta gccctagtt ccaacctagc cccaagatga actttccagt caaagagccc    1800
tcacaaccag ctatacatat ctgccttggc cactgccaag cagaaagatg acagacacca   1860
tcctaatatt tactcaaccc aaaccctaaa acatgaagag cctgccttgg tacattcgtg   1920
aactttcaaa gttagtcatg cagtcacaca tgactgcagt cctactgact cacaccccaa   1980
agcactcacc cacaacatct ggaaccacgg gcactatcac ataggtgt atatacagac     2040 ccttacacag caacagcact ggaaccttca caattacatc cccaaaacc acacaggcat    2100 aactgatcat acgcagcctc aagcaatgcc caaaatacaa gtcagacaca gcttgtcaga   2160
```

<210> SEQ ID NO 2
<211> LENGTH: 429
<212> TYPE: PRT
<213> ORGANISM: Mus musculus

<400> SEQUENCE: 2

```
Met Pro Asn Pro Arg Pro Ala Lys Pro Met Ala Pro Ser Leu Ala Leu
 1               5                  10                  15

Gly Pro Ser Pro Gly Val Leu Pro Ser Trp Lys Thr Ala Pro Lys Gly
                20                  25                  30

Ser Glu Leu Leu Gly Thr Arg Gly Ser Gly Gly Pro Phe Gln Gly Arg
            35                  40                  45

Asp Leu Arg Ser Gly Ala His Thr Ser Ser Leu Asn Pro Leu Pro
        50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
                100                 105                 110

Gln Thr Pro Val Leu Gln Val Arg Pro Leu Asp Asn Pro Ala Met Ile
            115                 120                 125

Ser Leu Pro Pro Pro Ser Ala Ala Thr Gly Val Phe Ser Leu Lys Ala
130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
    210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
            260                 265                 270

Ser Met Asp Lys Ser Ser Cys Cys Ile Val Ala Thr Ser Thr Gln Gly
        275                 280                 285
```

```
Ser Val Leu Pro Ala Trp Ser Ala Pro Arg Glu Ala Pro Asp Gly Gly
        290                 295                 300
Leu Phe Ala Val Arg Arg His Leu Trp Gly Ser His Gly Asn Ser Ser
305                 310                 315                 320
Phe Pro Glu Phe Phe His Asn Met Asp Tyr Phe Lys Tyr His Asn Met
                325                 330                 335
Arg Pro Pro Phe Thr Tyr Ala Thr Leu Ile Arg Trp Ala Ile Leu Glu
            340                 345                 350
Ala Pro Glu Arg Gln Arg Thr Leu Asn Glu Ile Tyr His Trp Phe Thr
        355                 360                 365
Arg Met Phe Ala Tyr Phe Arg Asn His Pro Ala Thr Trp Lys Asn Ala
370                 375                 380
Ile Arg His Asn Leu Ser Leu His Lys Cys Phe Val Arg Val Glu Ser
385                 390                 395                 400
Glu Lys Gly Ala Val Trp Thr Val Asp Glu Phe Glu Phe Arg Lys Lys
                405                 410                 415
Arg Ser Gln Arg Pro Asn Lys Cys Ser Asn Pro Cys Pro
            420                 425

<210> SEQ ID NO 3
<211> LENGTH: 1869
<212> TYPE: DNA
<213> ORGANISM: Homo sapien

<400> SEQUENCE: 3
gcacacactc atcgaaaaaa atttggatta ttagaagaga gaggtctgcg gcttccacac      60
cgtacagcgt ggttttcttt ctcggtataa agcaaagtt gttttgata cgtgacagtt      120
tcccacaagc caggctgatc cttttctgtc agtccacttc accaagcctg cccttggaca     180
aggacccgat gcccaacccc aggcctggca agccctcggc cccttccttg gcccttggcc     240
catccccagg agcctcgccc agctggaggg ctgcacccaa agcctcagac ctgctggggg     300
cccggggccc aggggaacc ttccagggcc gagatcttcg aggcggggcc catgcctcct     360
cttcttcctt gaacccccatg ccaccatcgc agctgcagct gcccacactg ccctagtca     420
tggtggcacc ctccggggca cggctgggcc ccttgcccca cttacaggca ctcctccagg    480
acaggccaca tttcatgcac cagctctcaa cggtggatgc ccacgccgg accctgtgc      540
tgcaggtgca cccctggag agcccagcca tgatcagcct cacaccacc accaccgcca     600
ctgggtctt ctcctcaag gcccggcctg gcctcccacc tgggatcaac gtggccagcc     660
tggaatgggt gtccagggag ccggcactgc tctgcacctt cccaaatccc agtgcaccca     720
ggaaggacag caccctttcg gctgtgcccc agagctccta cccactgctg gcaaatggtg     780
tctgcaagtg gcccggatgt gagaaggtct tcgaagagcc agaggacttc ctcaagcact     840
gccaggcgga ccatcttctg gatgagaagg gcagggcaca atgtctcctc cagagagaga     900
tggtacagtc tctggagcag cagctggtgc tggagaagga gaagctgagt gccatgcagg     960
cccacctggc tgggaaaatg gcactgacca aggcttcatc tgtggcatca tccgacaagg    1020
gctcctgctg catcgtagct gctggcagcc aaggccctgt cgtcccagcc tggtctggcc    1080
cccgggaggc ccctgacagc ctgtttgctg tccggaggca cctgtggggt agccatggaa    1140
acagcacatt cccagagttc ctccacaaca tggactactt caagttccac aacatgcgac    1200
cccctttcac ctacgccacg ctcatccgct gggccatcct ggaggctcca gagaagcagc    1260
ggacactcaa tgagatctac cactggttca cacgcatgtt tgccttcttc agaaaccatc    1320
```

-continued

```
ctgccacctg gaagaacgcc atccgccaca acctgagtct gcacaagtgc tttgtgcggg    1380
tggagagcga aaggggggct gtgtggaccg tggatgagct ggagttccgc aagaaacgga    1440
gccagaggcc cagcaggtgt tccaacccta cacctggccc ctgacctcaa gatcaaggaa    1500
aggaggatgg acgaacaggg gccaaactgg tgggaggcag aggtggtggg ggcagggatg    1560
ataggccctg gatgtgccca cagggaccaa gaagtgaggt ttccactgtc ttgcctgcca    1620
gggcccctgt tccccgctg gcagccaccc cctcccccat catatccttt gccccaaggc     1680
tgctcagagg ggccccggtc ctggccccag ccccaccctc cgcccagac acacccccca     1740 gtcgagccct gcagccaaac agagccttca caaccagcca cacagagcct gcctcagctg    1800
ctcgcacaga ttacttcagg gctggaaaag tcacacagac acacaaaatg tcacaatcct    1860
gtccctcac                                                            1869
```

<210> SEQ ID NO 4
<211> LENGTH: 431
<212> TYPE: PRT
<213> ORGANISM: Homo sapien

<400> SEQUENCE: 4

```
Met Pro Asn Pro Arg Pro Gly Lys Pro Ser Ala Pro Ser Leu Ala Leu
 1               5                  10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
         35                  40                  45

Asp Leu Arg Gly Gly Ala His Ala Ser Ser Ser Leu Asn Pro Met
  50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270
```

```
Ala Ser Ser Asp Lys Gly Ser Cys Cys Ile Val Ala Ala Gly Ser Gln
            275                 280                 285

Gly Pro Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
                340                 345                 350

Ala Pro Glu Lys Gln Arg Thr Leu Asn Glu Ile Tyr His Trp Phe Thr
                355                 360                 365

Arg Met Phe Ala Phe Phe Arg Asn His Pro Ala Thr Trp Lys Asn Ala
                370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
                420                 425                 430
```

<210> SEQ ID NO 5
<211> LENGTH: 23
<212> TYPE: DNA
<213> ORGANISM: Artificial Sequence
<220> FEATURE:
<223> OTHER INFORMATION: Primer for generation of mouse Fkh cDNA

<400> SEQUENCE: 5
gcagatctcc tgactctgcc ttc                                      23

<210> SEQ ID NO 6
<211> LENGTH: 23
<212> TYPE: DNA
<213> ORGANISM: Artificial Sequence
<220> FEATURE:
<223> OTHER INFORMATION: Primer for generation of mouse Fkh cDNA

<400> SEQUENCE: 6
gcagatctga caagctgtgt ctg                                      23

<210> SEQ ID NO 7
<211> LENGTH: 21
<212> TYPE: DNA
<213> ORGANISM: Artificial Sequence
<220> FEATURE:
<223> OTHER INFORMATION: Primer for generation of human Fkh cDNA

<400> SEQUENCE: 7
agcctgccct tggacaagga c                                        21

<210> SEQ ID NO 8
<211> LENGTH: 21
<212> TYPE: DNA
<213> ORGANISM: Artificial Sequence
<220> FEATURE:
<223> OTHER INFORMATION: Primer for generation of human Fkh cDNA -continued

```
<400> SEQUENCE: 8
gcaagacagt ggaaacctca c                                              21

<210> SEQ ID NO 9
<211> LENGTH: 20
<212> TYPE: DNA
<213> ORGANISM: Artificial Sequence
<220> FEATURE:
<223> OTHER INFORMATION: Primer for PCR amplification of mouse Fkh cDNA

<400> SEQUENCE: 9
ctacccactg ctggcaaatg                                                20

<210> SEQ ID NO 10
<211> LENGTH: 23
<212> TYPE: DNA
<213> ORGANISM: Artificial Sequence
<220> FEATURE:
<223> OTHER INFORMATION: Primer for PCR amplification of mouse Fkh cDNA

<400> SEQUENCE: 10
gaaggaacta ttgccatggc ttc                                            23

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide for hybridization reaction

<400> SEQUENCE: 11
atgcagcaag agctcttgtc cattgagg                                       28

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide for hybridization reaction

<400> SEQUENCE: 12
gcagcaagag ctcttttgtc cattgagg                                       28

<210> SEQ ID NO 13
<211> LENGTH: 22
<212> TYPE: DNA
<213> ORGANISM: Artificial Sequence
<220> FEATURE:
<223> OTHER INFORMATION: Primer for amplification of Fkh cDNA
<221> NAME/KEY: modified_base
<222> LOCATION: (7)...(7)
<223> OTHER INFORMATION: I

<400> SEQUENCE: 13
catcggngag atgctaagat gg                                             22

<210> SEQ ID NO 14
<211> LENGTH: 28
<212> TYPE: DNA
<213> ORGANISM: Artificial Sequence
<220> FEATURE:
<223> OTHER INFORMATION: Primer for amplification of Fkh cDNA

<400> SEQUENCE: 14
gaaaccagat tagtaagtat cttcgatt                                       28
```